(12) United States Patent
Gates

(10) Patent No.: US 12,002,180 B2
(45) Date of Patent: *Jun. 4, 2024

(54) IMMERSIVE ECOSYSTEM

(71) Applicant: Brightline Interactive, LLC, Alexandria, VA (US)

(72) Inventor: Tyler H. Gates, Arlington, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/849,123

(22) Filed: Jun. 24, 2022

(65) Prior Publication Data

US 2022/0327794 A1 Oct. 13, 2022

Related U.S. Application Data

(63) Continuation of application No. 16/985,529, filed on Aug. 5, 2020, now Pat. No. 11,373,383.

(60) Provisional application No. 62/883,016, filed on Aug. 5, 2019.

(51) Int. Cl.
| | |
|---|---|
| *G06T 19/20* | (2011.01) |
| *G02B 27/00* | (2006.01) |
| *G02B 27/01* | (2006.01) |
| *G06F 3/01* | (2006.01) |
| *G06N 20/00* | (2019.01) |

(52) U.S. Cl.
CPC .......... *G06T 19/20* (2013.01); *G02B 27/0093* (2013.01); *G02B 27/017* (2013.01); *G06F 3/013* (2013.01); *G06F 3/015* (2013.01); *G06F 3/016* (2013.01); *G06N 20/00* (2019.01)

(58) Field of Classification Search
CPC .... G06T 19/20; G06N 20/00; G02B 27/0093; G02B 27/017; G06F 3/013; G06F 3/015; G06F 3/016
USPC ........................................................ 345/633
See application file for complete search history.

(56) References Cited

U.S. PATENT DOCUMENTS

| | | | | |
|---|---|---|---|---|
| 8,893,164 | B1 * | 11/2014 | Teller ................. | G06Q 30/0252 725/12 |
| 2014/0162224 | A1 * | 6/2014 | Wallace ................. | G09B 5/06 434/219 |
| 2015/0206321 | A1 * | 7/2015 | Scavezze ............. | G06F 3/0485 345/633 |
| 2019/0073832 | A1 * | 3/2019 | Kim ...................... | G06T 19/006 |

* cited by examiner

*Primary Examiner* — Hai Tao Sun
(74) *Attorney, Agent, or Firm* — Duane Morris LLP

(57) ABSTRACT

An immersive training system, and method performed with such system, which comprises one or more sensors configured to measure at least one response of a user to a three-dimensional (3D) asset of a 3D rendering that is being rendered on a virtual reality (VR) display, the 3D rendering comprising a plurality of 3D assets. The immersive training system and method compares, in real time, the received measured response of the user to a corresponding predetermined user response value to the 3D asset and, based on the user response comparison and a generated user-customized dynamic decision matrix, modifies at least one of the plurality of 3D assets of the 3D rendering. A customized dynamic decision matrix is generated for each user based on, for example, a corresponding personal performance profile and a neural efficiency score.

20 Claims, 7 Drawing Sheets

IMMERSIVE ECOSYSTEM

CROSS-REFERENCE TO RELATED APPLICATION

This application is a continuation application of and claims priority to U.S. Non-Provisional patent application Ser. No. 16/985,529 filed on Aug. 5, 2020, the entirety of which is hereby incorporated herein by reference, which claimed priority to U.S. Provisional Patent Application No. 62/883,016, filed on Aug. 5, 2019, the entirety of which is herein incorporated by reference.

BACKGROUND

Virtual reality (VR) headsets allow users to visualize and experience an environment that is helpful to learning and understanding information that a user would not be able to absorb as effectively through simply watching a video or reading a manual. VR allows users to commit information to memory through actually experiencing scenarios as opposed to simply memorizing steps to take in such scenarios.

SUMMARY

According to an aspect of the present disclosure, an immersive ecosystem is provided. The immersive ecosystem comprises a virtual reality (VR) headset and one or more sensors. The VR headset is configured to display a selected one of a plurality of three-dimensional (3D) renderings to a user wearing the headset over a period of time. Each 3D rendering comprises a plurality of dynamic 3D assets. The one or more sensors are configured to measure a response of the user to one or more of the dynamic 3D assets of the 3D rendering. The immersive ecosystem further comprises a processor operably coupled to the VR headset, an artificial intelligence (AI) engine, and a first non-transitory computer-readable storage medium. The first non-transitory computer-readable storage medium is encoded with program code executable by the processor for providing the selected one 3D rendering to the VR headset during the period of time. The AI engine is operably coupled to a second non-transitory computer-readable storage medium that is configured to store predetermined response values, and predetermined time values within the period of time, for each of the plurality of dynamic 3D assets within each of the plurality of 3D renderings. The AI engine comprises a third non-transitory computer-readable storage medium encoded with program code executable by the AI engine. The program code is executable by the AI engine for receiving the measured user response to the one or more dynamic 3D assets of the selected one 3D rendering at a given time. The program code is further executable by the AI engine for comparing the received user response at the given time to the corresponding predetermined response value at the corresponding predetermined time value. The program code is further executable by the AI engine for, based on the comparison, modifying at least one of the plurality of dynamic 3D assets within the selected one 3D rendering. The program code is further executable by the AI engine for communicating the modified at least one of the plurality of dynamic 3D assets to the processor for providing within the selected one 3D rendering to the VR headset.

In some embodiments, the one or more sensors comprise one or more of functional near-infrared spectroscopy (fNIRS) technology, electroencephalogram (EEG) technology, electrocardiogram (ECG) sensors, heart rate sensors, motion capture (Mocap) sensors, body pressure sensors, and/or galvanic skin response (GSR) technology, or combinations thereof. In various embodiments, the fNIRS technology comprises one or more fNIRS sensors. In various embodiments, the EEG technology comprises one or more EEG sensors. In various embodiments, the GSR technology comprises one or more GSR sensors. In some embodiments, the measured user response comprises a measurement based on a user selection of the one or more dynamic 3D assets of the selected one 3D rendering. In some embodiments, the received measured user response comprises a value converted from the raw sensor measurement of the one or more sensors. In some embodiments, the value is cognitive load or cognitive attention or brain activation converted from the raw sensor measurement of one or more EEG sensors, and the third non-transitory computer-readable storage medium is further encoded with program code executable by the AI engine for computing a neural efficiency score for the user based on the cognitive load or cognitive attention value and a performance proficiency value for the user at the given time. In some embodiments, the immersive ecosystem further comprises an administrator interface configured to present one or more of the following data to an administrator: a visualization of the measured user response, a visualization of the value converted from the raw sensor measurement of the one or more sensors, and a video stream of the user. In some embodiments, the immersive ecosystem further comprises a forensics module configured to record the presented data.

In some embodiments, the predetermined response values are specific to the user. In some embodiments, the predetermined response values are adjustable based on an experience or training level of the user. In some embodiments, the immersive ecosystem further comprises a web application configured to execute on a computing device and further configured to enable the user to select an experience level, training level, or one of the plurality of 3D renderings.

In some embodiments, the processor, first non-transitory computer-readable storage medium, and second non-transitory computer-readable storage medium are components of one or more cloud servers, and the second non-transitory computer-readable storage medium is further configured to store the received measured user response to the one or more dynamic 3D assets of the selected one 3D rendering. In some embodiments, the third non-transitory computer-readable storage medium is further encoded with program code executable by the AI engine for generating a respective personal performance profile for each of a plurality of users including the user, and each personal performance profile is generated and updated based on stored measured user responses for the respective user and for the period of time. In some embodiments, the AI engine further comprises a respective dynamic decision matrix for each of the plurality of users based on the respective corresponding personal performance profile, and the third non-transitory computer-readable storage medium is further encoded with program code executable by the AI engine for modifying the at least one of the plurality of dynamic 3D assets based on the comparison and the respective dynamic decision matrix of the user.

In some embodiments, the modifying the at least one of the plurality of dynamic 3D assets step comprises at least one of: spatially moving the at least one dynamic 3D asset relative to the user, temporally moving the at least one dynamic 3D asset within the time period, replacing the current at least one dynamic 3D asset with a different dynamic 3D asset, adjusting the impact of the at least one dynamic 3D asset on other dynamic 3D assets within the selected one 3D rendering, adjusting the 3D atmospherics or 3D environment within the selected one 3D rendering including the at least one dynamic 3D asset, adjusting media and/or sound within the selected one 3D rendering including the at least one dynamic 3D asset, and adjusting the intensity of haptic output to the user based on the dynamic 3D asset. In some embodiments, the plurality of dynamic 3D assets comprise one or more of 3D atmospherics, 3D objects, 3D models, and 3D environments.

In some embodiments, the VR headset is configured to track eye movement of the user during the period of time and to transmit information related to the eye movement to the second non-transitory computer-readable storage medium. In some embodiments, the first non-transitory computer-readable storage medium is further encoded with program code executable by the processor for providing a portion of the selected one 3D rendering to the VR headset at a given time during the period of time and based on the transmitted information related to the eye movement. In some embodiments, the second non-transitory computer-readable storage medium is further configured to store predetermined eye movement values, and predetermined time values within the period of time, for each of the plurality of 3D renderings, and the first non-transitory computer-readable storage medium is further encoded with program code executable by the processor for providing a portion of the selected one 3D rendering to the VR headset at a given time during the period of time and based on the stored predetermined eye movement values, and predetermined time values, for the selected one 3D rendering. In some embodiments, the third non-transitory computer-readable storage medium is further encoded with program code executable by the AI engine for receiving the information related to said eye movement at a given time and comparing the received eye movement information at the given time to a corresponding predetermined eye movement value at a corresponding predetermined time value. In some embodiments, the third non-transitory computer-readable storage medium is further encoded with program code executable by the AI engine for, based on the comparison, modifying at least one of the plurality of dynamic 3D assets within the selected one 3D rendering and communicating the modified at least one of the plurality of dynamic 3D assets to the processor for providing within the portion of the selected one 3D rendering to the VR headset.

BRIEF DESCRIPTION OF THE DRAWINGS

Various aspects of the present disclosure will be or become apparent to one with skill in the art by reference to the following detailed description when considered in connection with the accompanying exemplary non-limiting embodiments.

Figure 1:
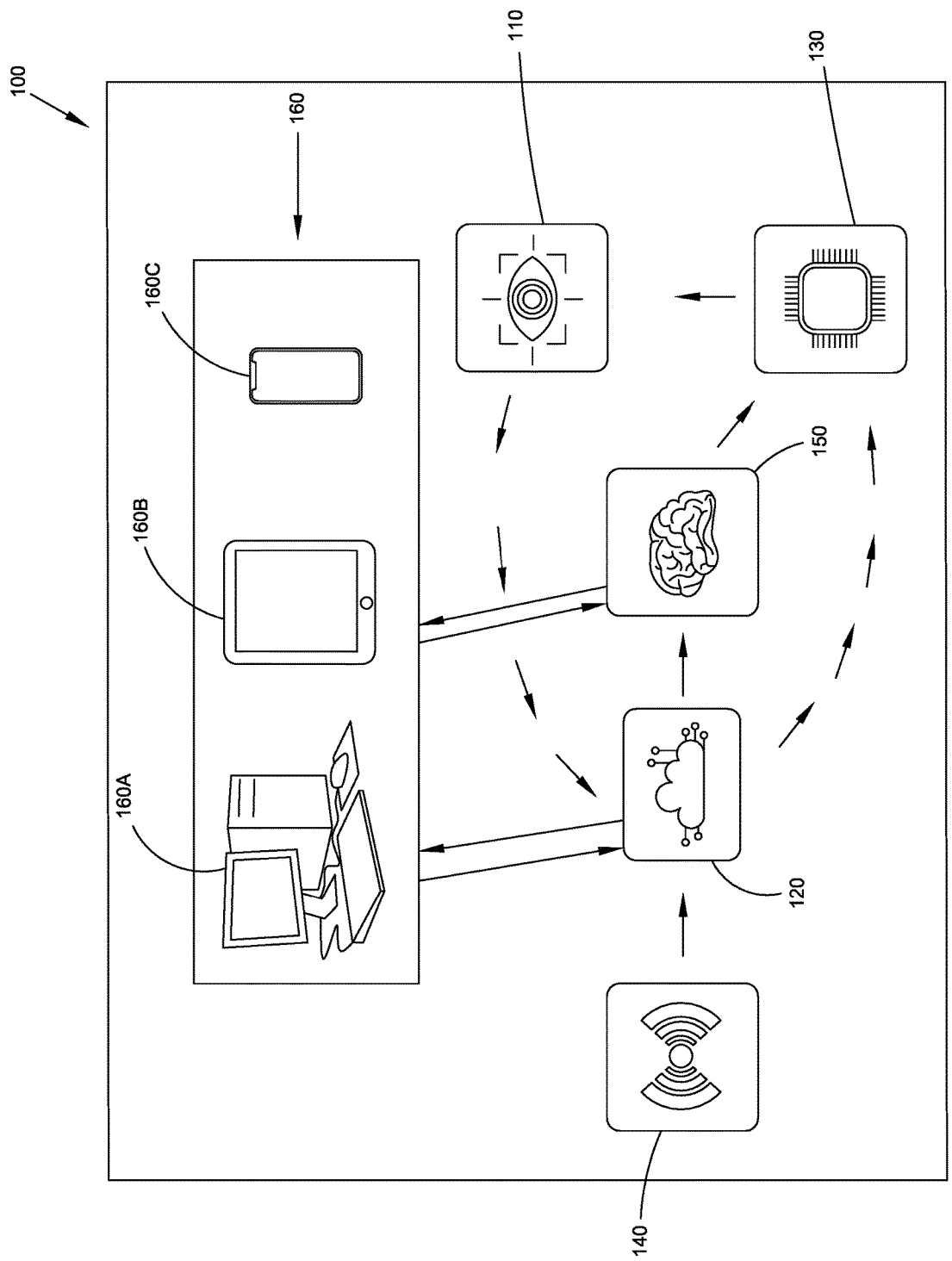
FIG. 1 is a block diagram of an immersive ecosystem according to some embodiments of the present disclosure.

The present application discloses illustrative (i.e., example) embodiments. The claimed inventions are not limited to the illustrative embodiments. Therefore, many implementations of the claims will be different than the illustrative embodiments. Various modifications can be made to the claimed inventions without departing from the spirit and scope of the disclosure. The claims are intended to cover implementations with such modifications.

DETAILED DESCRIPTION

For the purposes of promoting an understanding of the principles of the disclosure, reference will now be made to a number of illustrative embodiments in the drawings and specific language will be used to describe the same.

Various aspects of the present disclosure will be or will become apparent to one of skill in the art by reference to the following detailed description when considered in connection with the accompanying exemplary non-limiting embodiments.

Typically, the performance of complex tasks requires the integration of various mental resources, such as task-related knowledge, working memory, attention, and decision making. Cognitive load in this sense is commonly attributed to the misallocation of information without conventional recognition of situational relevance and the timing and accuracy of information as it is displayed. The inventor has determined that the immersive ecosystem described herein provides solutions to analyze and manage real-time cognitive load (or cognitive attention or brain activation) in simulations through both neural, physiological, and performance proficiency feedback loops. Further, the inventor has determined that the immersive ecosystem provides unique solutions to users, administrators, and organizations across a variety of industries including, but not limited to, defense and intelligence, commercial brands, health, and human performance, as described herein.

Figure 4:
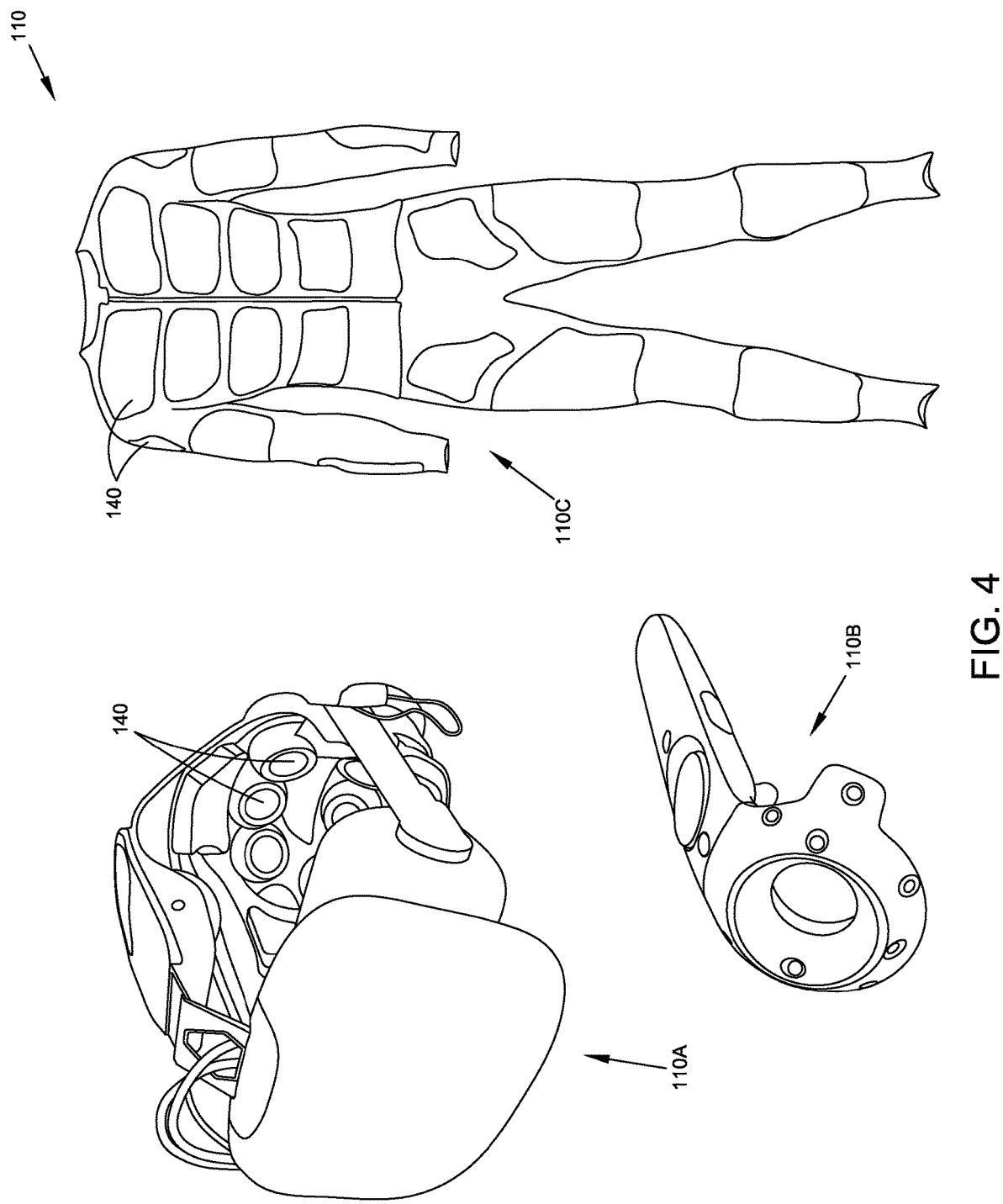
FIG. 4 is a diagram showing an example of virtual reality technology according to some embodiments of the present disclosure.

FIG. 1 illustrates a block diagram of an immersive ecosystem 100 that facilitates database and sensor-driven virtual reality (VR) scenarios that enable users to participate in experiential learning, evaluation, and treatment. In various embodiments, the immersive ecosystem 100 facilitates database and sensor-driven augmented reality (AR) scenarios, and/or mixed reality (XR) scenarios, which enable users to participate in experiential learning, evaluation, and/or treatment. The immersive ecosystem 100 may be especially useful for training (e.g. first responder (e.g. paramedic, law enforcement, firefighter) training, disaster response training, military training (e.g. for explosive ordnance disposal), human resources (HR) training, block chain training, manufacturing training), fitness evaluation (e.g. professional assessments for pilots and surgeons), and treatment sessions (e.g. addiction treatment). The immersive ecosystem 100 comprises VR technology 110 that enables users to visualize a VR scenario. FIG. 4 illustrates non-limiting examples of VR technology 110, which may include a VR headset 110A, VR hand controllers 110B, and haptic paraphernalia (e.g. a haptic bodysuit 110C). VR technology 110 may be equipped with sensors 140 to measure user responses. Similar AR and XR technology may be substituted in the immersive ecosystem during AR and XR scenarios, respectively. The VR headset 110A (shown in FIGS. 4, 5A, and 5B) illustrates one non-limiting example of a VR headset 110A and sensor 140 system. Multiple other configurations of sensor 140 systems and VR headset 110A may be utilized in immersive ecosystem 100. These other configurations may include various placements and designs of the goggles 500 and other components of the VR headset 110A, as well as various locations, types, configurations, shapes, sizes, and numbers of sensors 140.

Additionally, the immersive ecosystem 100 may utilize screen-based interactive modalities (e.g. tablet (e.g. 160B), PC desktop (e.g. 160A), mobile phone (e.g. 160C) as an administrator interface to display information (e.g. on a dashboard) to a user and/or receive inputs into the immersive ecosystem from administrators (e.g., trainer, supervisor, doctor, fitness instructor, hospital administrator, police/fire chief, senior military officer/enlisted, etc.) In various embodiments, the immersive ecosystem may also provide support for multi-device networking. For example, the artificial intelligence (AI) engine 150 may communicate data to the processor 130 for transmission to primary VR technology 110 (e.g. to VR headset (110A, FIG. 4), to haptic bodysuit (110C, FIG. 4), etc.) and may also provide near real-time updates and feedback to an assigned administrator interface dashboard (e.g., tablet 160B, PC desktop 160A, mobile phone 160C) or other screen-based system acting as an administrator interface control system. Multiple VR technology hardware configurations may exist in a variety of setups depending on the use case.

The VR technology 110 (or AR technology, XR technology) may be used to measure data such as eye tracking (to determine where a user is actively looking within the VR headset and related to a particular VR scenario) and position mapping data (to determine a user's position within a three-dimensional (3D) rendering). Eye-tracking technology may be native to the VR headset hardware (e.g. cameras embedded in the VR headset). Position mapping data (e.g. 3D spatial data) may be measured by a sensor 140 in the VR headset (e.g. 110A, FIGS. 4, 5A-5B) that maps the virtual position orientation of the VR headset inside the virtual environment. For example, a VR headset (e.g. 110A, FIGS. 4, 5A-5B) may include an integrated eye tracker (e.g. fovea tracker). Eye tracking data and/or position mapping data may be transmitted to a database 120 within the immersive ecosystem 100. The VR technology 110 may be configured to track eye (e.g. fovea) movement of the user during a period of time and to transmit information related to said eye movement to database 120 and/or processor 130.

The database 120 and/or processor 130 may be local (e.g. local to VR technology 110) or cloud based. In some embodiments, the immersive ecosystem 100 may be a closed system where data is locally processed and stored (e.g. respectively by processor 130 and in database 120 local relative to VR technology 110). The inventor has identified that the advantages of a closed system include enhanced security. In some embodiments, the immersive ecosystem 100 may be an open system that interacts with and receives data from different virtual environment simulations going on remote relative to each other (e.g. over a geographic area, all over the world). In such an open system, data may be processed and stored in the cloud (e.g. respectively by processor 130 and in database 120). The inventor has identified that advantages of an open system include the ability to process more information and the ability to process it against information from other virtual environment simulations.

A VR headset (e.g. 110A, FIGS. 4, 5A-5B) may be configured to display one of a plurality of 3D renderings (e.g. 600, FIG. 6) to a user wearing the headset over a period of time. A user may view the display of a 3D rendering through goggles 500 in VR headset 110A, illustrated in FIG. 5B. Non-limiting examples of 3D renderings may include an environment with a live bomb (e.g. for explosive ordnance disposal training) or with a conveyor belt (e.g. for manufacturing training and/or supply chain training), an operating room and surgery simulation (e.g. for assessment of an advanced age surgeon's dexterity and overall surgical capabilities), or a treatment environment with triggering and recovery scenarios specific to a user (e.g. for opioid addiction treatment).

The immersive ecosystem 100 may further comprise a processor 130 such as a computer processing unit (CPU). The processor 130 may be operably coupled to a headset (e.g., VR headset, AR headset, XR headset) (e.g. 110A) and a non-transitory computer-readable storage medium. The non-transitory computer-readable storage medium may be encoded with program code executable by the processor 130 for providing a selected 3D rendering (e.g. 600) to a VR headset (e.g. 110A) during a period of time. The non-transitory computer-readable storage medium may be a component of a cloud server. The non-transitory computer-readable storage medium may comprise a gaming engine, and/or a database, that may provide a VR 3D rendering (e.g. 600). This non-transitory computer-readable storage medium may be further encoded with program code executable by the processor 130 for providing a portion of the selected 3D rendering (e.g. 600) to a VR headset (e.g. 110A) at a given time based on the transmitted information related to the user's eye movement. This non-transitory computer-readable storage medium may be further encoded with program code executable by the processor 130 for providing a portion of the selected one 3D rendering (e.g. 600) to a VR headset (e.g. 110A) at a given time based on stored predetermined eye movement values and predetermined time values for the selected one 3D rendering (e.g. 600). Providing only a portion of the selected one 3D rendering to a VR headset (e.g. 110A) may allow other portions of the 3D rendering outside of a user's view to be put to rest (i.e. not actively updated when not in view, or at a lower resolution), which enables faster local processing and more complex 3D renderings. Database 120 may be further configured to store predetermined eye movement values and predetermined time values within the period of time for each of the plurality of 3D renderings. Each 3D rendering (e.g., VR 3D rendering, AR 3D rendering, XR 3D rendering) may comprise a plurality of dynamic 3D assets (e.g. 610). The dynamic 3D assets (e.g. 610) may comprise one or more of 3D atmospherics, 3D objects, 3D models, 3D environments, and 3D representation of context.

The immersive ecosystem 100 may further comprise one or more sensors 140 that are configured to measure a response of a user to one or more dynamic 3D assets (e.g. 610) within a 3D rendering (e.g. 600). Non-limiting examples of the sensors 140 include functional near-infrared spectroscopy (fNIRS) sensors, electroencephalogram (EEG) sensors, electrocardiogram (ECG) sensors, heart rate sensors, galvanic skin response (GSR) sensors, motion capture (Mocap) sensors, body pressure sensors (e.g. finger pressure sensors), and positron emission tomography (PET) sensors. In various embodiments, one or more Mocap sensors may measure body positioning of a user in space relative to the 3D rendering. One or more of these sensors 140 can be integrated into head-mounted displays (HMDs) (e.g. in a VR headset 110A, FIGS. 4, 5A) and various non-HMD form factors such as, for example, helmets, hard hats, baseball caps, clothing (e.g. haptic body suit 110C (FIG. 4)), accessories, etc. A user's (e.g. trainee's) physiological data (e.g. ECG and/or heart rate) can be monitored through discrete, external peripheral sensors that can be outfitted on the user by an administrator. A user's physiological data (e.g. EEG, GSR, ECG and/or heart rate data) can be measured by one or more sensors 140 and, for example, transferred and viewed in near real-time at an administrator interface (e.g. 160).

In various embodiments, users may also be outfitted with physical trackers to capture their motion in space. For example, Mocap data can be mapped to a VR HMD for real-time visualization of user motion in a 3D rendering. In various embodiments, a physical tracker may include one or more accelerometers calibrated in one or more motion axes. A device comprising a plurality of sensors 140 (e.g. a haptic body suit 110C, FIG. 4) may also be included in the immersive ecosystem 100. The sensors 140 may provide the sensor data to database 120. In some embodiments, and as described herein (e.g. FIG. 3), the immersive ecosystem 100 may use an adaptive algorithm designed specifically to utilize data from sensors 140 (and/or data derived from such sensor data and performance proficiency such as a neural efficiency score). The inventor has determined that such an adaptive algorithm helps instructors or other personnel evaluate a user (e.g. a trainee) during a VR scenario (or AR scenario or XR scenario) and further predict affecting patterns and stressors on performance and the training factors that induce these patterns in real time. The inventor has determined that the immersive ecosystem 100 provides a baseline infrastructure with capability to ingest additional neurological, physiological, and performance data types as the need may arise. The inventor has also determined that the open data architecture provided by the immersive ecosystem 100 makes the ecosystem infinitely customizable with the ability to scale across user bases.

The immersive ecosystem 100 further comprises an AI engine 150. One non-limiting example of an AI engine 150 is a performance adaptive virtual engine (PAVE). The processor 130 may be operably coupled to the AI engine 150. The AI engine 150 may also be operably coupled to a non-transitory computer-readable storage medium such as the database 120. Database 120 may be configured to store predetermined response values (e.g. a stress level threshold, proficiency threshold, neural efficiency threshold) for a user and predetermined time values within a period of time for dynamic 3D assets within 3D renderings. In a closed system, the predetermined response values (e.g. stress level threshold, proficiency threshold, neural efficiency threshold) may be required to be pre-programmed in database 120. In an open system where database 120 is cloud based, the predetermined response values may be updated and compared to response values in simulation environments remote from each other. For example, a proficiency threshold may be a threshold of objective correctness of a user's (or group of users') decision (e.g. as selected at a controller) within a particular 3D rendering for a given time. Database 120 may be a component of a cloud server. The AI engine 150 may comprise a non-transitory computer-readable storage medium, such as an AI database, encoded with program code that is executable by the AI engine for method 200, shown in FIG. 2.

In various embodiments, an EEG sensor 140 (e.g. external EEG sensor peripheral) may be integrated into a VR headset (e.g. 110A), and/or into a HMD of a VR headset, in order to provide a real-time neurological response input (e.g. cognitive load, cognitive attention, brain activation) of a user (e.g. trainee) to a real-time neural efficiency calculator. Brain activation is a measurement of the heightened firing of cells in evaluated areas of a user's brain in response to some stimulus (e.g. the measured area of a user's brain that is evaluated as having heightened activity is responding internally or is being affected by other regions of the brain, or that region itself is affecting other regions of the brain). Cognitive load is a measurement related to heightened stress response, due to the incorporation and increase in environmental and other stimuli affecting a user where this increase in stimuli impacts cognitive attention, typically (as observed by the inventor) in a negative way. Cognitive attention is a measurement related to cognitive load but focused on the ability of a user to concentrate on specific stimuli while ignoring other incoming affecting stimuli. As used herein, neural efficiency is an objective, real-time measurement of a user's neurological response (e.g., cognitive load, cognitive attention, brain activation) versus task performance proficiency (e.g. a measurement of the correctness of a user's decision (e.g. as selected at a user controller (110B)) at a given time) within a particular 3D scenario. In various embodiments, a user's neural efficiency score conveys the ability of the user to perform tasks well/not well in a given 3D scenario based on the relationship of cognitive load, cognitive attention and/or brain activation at a given moment in time in such scenario. In various embodiments, AI engine 150 may compute a user's neural efficiency score with real-time EEG sensor data and real-time proficiency data throughout a particular 3D scenario. The inventor has determined that, in general, more proficient users show lower brain activation, lower cognitive load, and higher cognitive attention than less proficient users when performing the same cognitive tasks in the same 3D scenario.

The inventor has determined that the immersive ecosystem 100, and specifically the immersive ecosystem's provision of objective metrics (e.g., proficiency threshold, neural efficiency) to administrators, enables administrators (e.g., military, corporate/hospital/police/fire management, etc.) to objectively compare the value of various VR, AR, or MR training simulation systems. The inventor has observed that the military and law enforcement, in particular, have limited time and money to spend on training, and there is a need to move servicemen and women through training programs efficiently and effectively. The inventor has also observed that training instructors' time is expensive and limited, and instructors often have to subjectively estimate and evaluate performance. The inventor has determined that the absence of a quantifiable, objective perspective leaves the training instructor to make a series of abstractions based on secondary elements such as body language and contextual information. For example, when evaluating a trainee, instructors cannot know directly what is going on in the trainee's head. The inventor has observed that, to overcome this information gap, instructors may use inferential details like body language and patterns of decision making, among other inferential details, to discern the actual performance of the trainee. Furthermore, the inventor has also observed that instructors can speak with a trainee to get a better perspective and validate the instructors' assumptions, but the trainee might not know how they felt, not remember, underplay their actual disposition, and/or accidentally provide incorrect information. The inventor has further observed that, with miscommunication being a hallmark of operational inefficiency, and military/law enforcement training instructors having little time and limited information to make important decisions, such deficiencies lead them to resort to standardized training protocols, resulting in expensive "overtraining" for proficient trainees and risky "undertraining" for those trainees who need more time or resources.

Traditional methods for virtual and/or simulated assessment of trainees across civilian and military industries provide no quantitative data of the effects of the simulations on such trainees, and the resulting assessment protocols fail to adequately and objectively validate trainee progression. Significantly, the inventor has observed that the decision-making process to adopt a new training technique is especially challenging when trying to compare trainee-learning outcomes in terms of competency and technical performance. For example, the inventor has observed that if trainee A scores high on an easy training level, and trainee B scores low on a high difficulty level, it is difficult to for an instructor and/or administrator to determine which trainee (A or B) performed better since the difficulty levels vary. The inventor has observed that this assessment problem carries over into the issue of using a VR (or AR or XR) simulation trainer versus the traditional learning and training materials. However, the inventor has determined that simulation training with the immersive ecosystem 100 offers facilities in which cognitive load and cognitive performance can be observed and measured throughout particular 3D scenarios in a safe, objective, and controlled environment at a low cost. For example, as described herein, EEG sensors in the immersive ecosystem can provide a real-time sensor measurement that may be used as an input in determining a neural efficiency score for a trainee, and this neural efficiency score can distinguish between which trainees have mastered the material (e.g. a particular 3D scenario) and which trainees need more practice. The inventor has determined that this tool that assesses cognitive load and cognitive performance (resulting with a neural efficiency score) can empower instructors to make more informed decisions over key problem areas faster, at a lower cost, and with greater accuracy.

As described herein, by comparing an individual trainee's real-time cognitive load to their performance and their expected performance throughout a particular 3D scenario, the AI engine 150 can derive a neural efficiency score. The inventor has determined that neural efficiency scores help administrators (e.g., military, law enforcement, etc.) identify which VR training setups, system configurations, and scenarios help trainees master the training material most efficiently and which VR training setups, system configurations, and scenarios lag behind. The inventor has also determined that these neural efficiency scores can also be applied to everyday training to assess a trainee's neural performance relative to expected neural efficiency scores. Trainees whose neural efficiency scores are below expectations might struggle with the training and require more sessions in a VR simulator or conventional simulator. On the other hand, trainees whose neural efficiency scores exceed expectations may be accelerated through the training process, saving time and simulator resources which are scarce in most cases. Additionally, the inventor has determined that these neural efficiency scores may allow a trainee to review his or her own performance and gain insights into how to improve for the next evaluation. The inventor has further determined that these neural efficiency scores will allow administrators (e.g., military, law enforcement, etc.) to more objectively compare particular training setups, system configurations, and scenarios in terms of cost, time, and value (i.e. quality advantages).

In some embodiments, the immersive ecosystem may also include a virtual training assessment tool (VTAT) operating across VR technology 110, AI engine 150, processor 130 and database 120, and receiving real-time inputs from, for example, real-time sensors 140. As described above, the VTAT may provide neural insights (e.g. neural efficiency) that can show the progression of a user (e.g. a military trainee) over time throughout the duration of a 3D scenario (e.g. a VR, AR, or XR training module). In various embodiments, the core data processing and assessment software used for VTAT is configured to power the data transmission loop from a neurological sensor form factor (e.g. sensors 140 deployed in a VR headset 110A) and is configured to support the use of visualization modalities (e.g. dynamic 3D assets in 3D renderings displayed in VR headset 110A) and user performance proficiency used to evaluate real-time neural analytics (e.g. neural efficiency) in particular 3D scenarios. In various embodiments, the VTAT may be configured to ingest unique neurological performance data in real-time, translate that data into digital symbols, and visualize the translated data on an administrator interface (e.g. an analytics dashboard available to instructors and/or trainees) (e.g. 160A, 160B, 160C). In various embodiments, as described herein, the VTAT may allow instructors to understand how user trainees are reacting neurologically in a VR/AR/XR training environment, and, leveraging video streams from trainee VR/AR/XR 3D scenarios, correlate neural data spikes against trainee actions in a given virtual environment. In various embodiments, as described herein, the VTAT may supply instructors with neurological measurements that can be applied to a trainee's personal performance profile (e.g. including a lifetime scorecard), which is described above and with respect to FIG. 2 below. Utilizing this data, instructors can see progression and can use these real-time neurological measurements, and real-time proficiency data, to determine a trainee's neural efficiency score during a particular VR/AR/XR 3D scenario (e.g. a particular training simulation session). Additionally, as described herein, particular 3D scenario performance may be recorded (e.g. by recording cameras in a HMD of VR headset 110A for storage in database 120), and subsequently rewound or reviewed (e.g. via an administrator interface 160A, 160B, 160C) during a debrief or after-action review (AAR) session after the trainee has completed a VR/AR/XR training module.

The immersive ecosystem 100 may further comprise a web application configured to execute on a computing device (e.g. via VR technology 110, via administrator interface 160). The web application may be further configured to enable the user/administrator to select (e.g. via hand controller 110B and VR headset 110A, via administrator interface 160) an experience level, training level, and/or one of the plurality of 3D renderings. The web application may be further configured to enable the user/administrator to set a predetermined response value (e.g. a stress level threshold, proficiency threshold) to be used by the AI engine 150. The web application may be further configured to enable a user, trainer, or administrator to control the intensity (e.g. stress intensity) of a training, evaluation, or treatment session.

Figure 2:
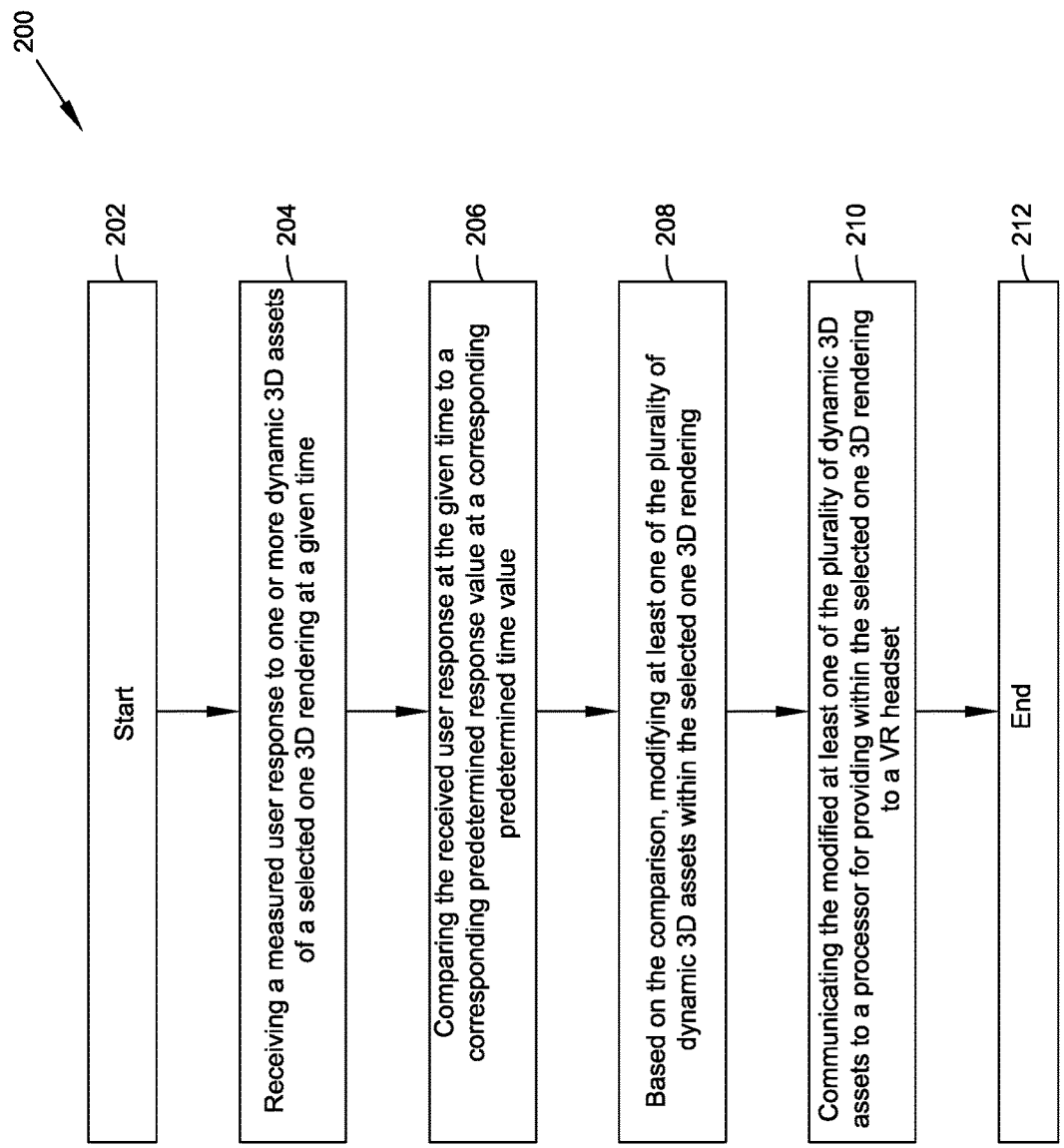
FIG. 2 is a flow chart illustrating an artificial intelligence engine-implemented method according to some embodiments of the present disclosure.

FIG. 2 is a flow chart illustrating an example of a method 200 implemented by AI engine 150, wherein the AI engine 150 modifies 3D assets dynamically and based on user responses (e.g., proficiency, physiological response, neural response, etc.). Method 200 begins at step 202. In an example, the user may be a surgeon (e.g. experienced but advanced age surgeon) undergoing an evaluation of his/her dexterity and overall surgical capabilities in an AR and/or XR 3D scenario.

At step 204, the AI engine 150 may receive a measured user response (e.g. a user's hand's pressure on a scalpel, sweat, stress level) to one or more dynamic 3D assets (e.g. a patient with appendicitis) of a selected one 3D rendering at a given time in the AR and/or XR scenario. The user response may comprise a measurement based on a user selection of one or more dynamic 3D assets within a selected 3D rendering. The received measured user response may comprise a value converted from a raw sensor measurement of the one or more sensors 140. For example, EEG sensors may provide a raw sensor measurement that, along with task performance proficiency (e.g. correctness and accuracy of a user's decision (e.g. as selected with a scalpel at a given time)), may be converted to a neural efficiency score by AI engine 150 for the user. The AI engine 150 may present this neural efficiency score, the raw sensor measurement, and/or the task performance proficiency measurement, in near real time on an analytics dashboard available to an instructor or personnel tasked with evaluating a user (e.g., via administrator interface 160). Database 120 may be further configured to store the received measured user response to one or more dynamic 3D assets of the selected one 3D rendering and/or during the corresponding time period of the 3D scenario. The non-transitory computer-readable storage medium of the AI engine 150 may be further encoded with program code executable by the AI engine 150 for generating a respective personal performance profile for each of a plurality of users, including the user. Each personal performance profile may be generated and updated based on stored measured user responses for the respective user and for the period of time within the particular 3D scenario. The AI engine 150 may further comprise a respective dynamic decision matrix for each of the plurality of users based on the respective corresponding personal performance profile. The dynamic decision matrix may be interconnected with environmental, physiological, cognitive, and performance analytics (e.g. with a neural efficiency score). The dynamic decision matrix for a given user may be subject to change based on the individual and collective analytics gathered over a period of time and/or based on the neural efficiency score computed for the user.

At step 206, the AI engine 150 may compare the received user response at the given time to the corresponding predetermined response value at the corresponding predetermined time value (e.g. comparing a surgeon's actual hand pressure on a scalpel with the predetermined, appropriate pressure). The predetermined response values may be objective across a group of users. The predetermined response values may be specific to a user. The predetermined response values may be adjustable based on an experience or training level of the user and/or based on a neural efficiency score computed for the user. The non-transitory computer-readable storage medium of the AI engine 150 may be further encoded with program code executable by the AI engine 150 for modifying the at least one of the plurality of dynamic 3D assets based on the comparison and the respective dynamic decision matrix of the user.

At step 208, based on the comparison in step 206, the AI engine 150 may modify at least one of the plurality of dynamic 3D assets within the selected one 3D rendering. For instance, in a surgical evaluation AR and/or XR 3D scenario, if the surgeon (user) applies the appropriate scalpel pressure and exhibits an appropriate stress level as compared to the predetermined pressure and stress level, the AI engine 150 may significantly worsen the condition of the patient (dynamic 3D asset) to assess the surgeon's dexterity and surgical capabilities during a patient crisis.

Further examples of the modifying the at least one of the plurality of dynamic 3D assets step in a given 3D scenario (e.g. explosive ordinance disposal training scenario) may comprise at least one of: spatially moving the at least one dynamic 3D asset relative to the user (e.g. moving a bomb location); temporally moving the at least one dynamic 3D asset within the time period (e.g. delaying the time of a bomb detonation); replacing the current at least one dynamic 3D asset with a different dynamic 3D asset (e.g. replacing the bomb with rocks); adjusting the impact of the at least one dynamic 3D asset on other dynamic 3D assets within the selected one 3D rendering (e.g. making the bomb kill no one when detonated instead of killing 3 people); adjusting the 3D atmospherics or 3D environment within the selected one 3D rendering including the at least one dynamic 3D asset (e.g. changing the weather from sunny to stormy); adjusting media and/or sound within the selected one 3D rendering including the at least one dynamic 3D asset (e.g. adding high levels of background noise to the 3D rendering); adjusting the intensity of haptic output to the user based on the dynamic 3D asset (e.g. changing the level of pain inflicted on the user by the electrodes in a haptic body suit (e.g. 110C) when a bomb is detonated near the user); adjusting a user's virtual position within the selected one 3D rendering; shortening or lengthening the selected one 3D rendering; altering the speed of the selected one 3D rendering; altering the intensity of the selected one 3D rendering.

At step 210, the AI engine 150 may communicate the modified at least one of the plurality of dynamic 3D assets to the processor for providing within the selected one 3D rendering to the VR, AR and/or XR headset (e.g. 110A). The non-transitory computer-readable storage medium of the AI engine 150 may be further encoded with program code executable by the AI engine 150 for receiving the information related to a user's eye movement at a given time and comparing the received eye movement information at the given time to a corresponding predetermined eye movement value at a corresponding predetermined time value for the particular 3D rendering. The non-transitory computer-readable storage medium of the AI engine 150 may be further encoded with program code executable by the AI engine 150 for, based on the comparison, modifying at least one of the plurality of dynamic 3D assets within the selected one 3D rendering and communicating the modified asset to the processor 130 for providing within the portion of the selected one 3D rendering to the VR, AR and/or XR headset (e.g. 110A) (e.g. activating a bomb when it comes into the user's line of sight).

Method 200 ends at step 212.

As mentioned previously, in some embodiments, an exemplary 3D rendering may include an HR training environment. When coupled with holographic telepresence technology, the immersive ecosystem 100 may be particularly useful for HR training. Holographic telepresence technology may enable a VR headset (e.g. 110A) to display a 3D rendering comprising a hologram (derived from a depth image) of an HR administrator giving a presentation remotely. The presentation may also be pre-recorded. With eye tracking sensors, the immersive ecosystem 100 may be able to track the user's attention span by monitoring where a user is looking at a particular time and comparing that data to baseline data on where the user should be looking at that time and for a particular 3D rendering. The inventor has identified that allowing HR administrators to present remotely while providing users with an experiential, augmented reality (AR) training environment in a 3D capacity will save companies money on travel expenses without detracting from the user's immersive training experience. Additionally, this remote training capability will benefit trainees affected by the COVID-19 pandemic by providing an effective remote option for training and evaluation.

As mentioned previously, in some embodiments, an exemplary 3D rendering may include a block chain training environment. Similar to the previous example, the immersive ecosystem 100 may use holographic telepresence technology to enable a VR headset (e.g. 110A) to display a 3D rendering comprising a hologram (derived from a depth image) of a technical expert on block chain technology, who is giving (or previously gave) a presentation remotely. The presentation may be pre-recorded to enable the technical expert to develop graphics (e.g. 3D blocks in a block chain) that may be superimposed as dynamic 3D assets within the 3D rendering. This may enable the user to pause the presentation and interact with and examine one or more blocks of the block chain (e.g. pick up a block and inspect the contents, such as one or more dynamic 3D assets representing binary encryption code, or remove a block from the chain to visualize the consequences of removing a block through other dynamic 3D assets) to provide the user with an enhanced learning experience that he/she can participate in at his/her own individual pace. This exemplary embodiment may be applicable to similar emerging technology training and is not limited to block chain technology training.

As mentioned previously, in some embodiments, an exemplary 3D rendering may include a first responder training environment. For example, the 3D rendering may simulate a transformer explosion or active shooter scenario where the user is being trained as a first responder. The immersive ecosystem 100 may enable the user to participate in a variety of 3D renderings as often as necessary, allowing the user to experientially develop a "firefighters intuition" in an augmented reality, 3D environment. In some embodiments, and as illustrated in examples in FIGS. 4 and 5A-5B, the VR technology 110 may include a VR headset (e.g. 110A) and a haptic body suit (e.g. 110C) worn by the user while the user also interacts with dynamic 3D assets in the 3D rendering with non-virtual equipment (e.g. a service weapon). If, during the 3D scenario, the user makes a mistake that could lead to them being shot in the active shooter 3D rendering, the haptic body suit (e.g., 110C, FIG. 4) may simulate real pain (through the use of electrodes at the location of the simulated injury) to form an association between the user's mistake and pain in the user's memory in order to more effectively train them as a first responder.

As described above, in some embodiments, an exemplary 3D rendering may include an environment with one or more triggers specific to a user for the treatment of the user's addiction (e.g. opioid addiction). "Affect labeling" is a psychological protocol that is currently being used to help manage emotional experiences through imagery, both static and video. The efficacy and underpinning mechanisms of this technique have been established at the neuroscience level in the laboratory using fMRI (functional magnetic resonance imaging) techniques in clinical studies. The inventor has identified that an immersive ecosystem 100 allows for the integration of affect labeling in a more meaningful way using immersive, realistic, and simulated environments to contextually visualize data in real time.

In order to utilize an immersive ecosystem 100 for treating opioid addiction, a patient may report to a specialist's office where the VR technology 110 (e.g. a VR headset (e.g. 110A) and one or more VR hand controllers (e.g. 110B)) may be set up. The patient may put on the VR headset (e.g. 110A) and pick up the one or more VR hand controllers (e.g. 110B). Once the specialist prompts the program, the patient may be taken to a login screen to enter a unique identifying number to direct them to their personal performance profile. During their first session and in setting up a personal performance profile, the patient may go through a short tutorial of course objectives and a tutorial for navigating within the VR session. Once a personal performance profile has been confirmed, the patient may enter a 3D rendering (e.g. a virtual lobby) and course options may be displayed as determined by the subject matter expert or specialist.

During an initial data collection phase, a VR headset (e.g. 110A) may rapidly deliver dynamic 3D assets within a 3D rendering to the patient user configured to trigger unconscious and unbiased brain stimulation of the patient user measured using one or more sensors. For example, fNIRS sensors may be integrated into the VR headset (e.g. 110A) to assess stress levels by analyzing for changes in the blood flow and oxygenation levels in the brain. In some embodiments, EEG sensors may be integrated into the VR headset (e.g. 110A) to assess cognitive activity throughout the simulation. In various embodiments, this method of initial data collection from peripheral sensors is referred to as edge computing. After the initial data collection phase, the AI engine 150 may direct the patient user to a personalized, triggering 3D rendering to test the patient's determined triggered scenarios. The patient user may be able to experience a variety of settings within the triggering 3D rendering to mimic possible iterations of life-like scenarios. Specific user responses may be tested and analyzed such as, for example, neurological state, focus areas, and actionable decisions. While the patient user is viewing the triggering 3D rendering, the patient user may be able to interact both physically with dynamic 3D assets (e.g. objects) and vocally with dynamic 3D assets (e.g. people) and walk around in a given space (3D rendering environment). Using a microphone (e.g. integrated into a VR headset), a patient user may be able to communicate with virtual humans in the 3D rendering using simple conversation and predetermined communication paths.

The personal performance profile may be stored in database 120 and managed by the AI engine 150. The personal performance profile may comprise pre-assessment metadata such as the patient user's name, demographic information, addiction history, and the patient's emotional and personality profile. The personal performance profile may further comprise detailed program objectives, results, and feedback as well as detailed program neurological responses (user responses) and feedback. The specialist may be able to access the patient user's personal performance profile, including key performance indicators (e.g. neural efficiency), on a data visualization tool (e.g. analytics dashboard) accessible through a secure portal (e.g. using an administrator interface 160). The specialist may be able to monitor (e.g. using an administrator interface 160) the patient user's performance in the 3D rendering in near real-time, receive immediate feedback, and manually set parameters for particular patients.

The immersive ecosystem 100 may include two main types of interactions: (1) active decision analytics and (2) passive cognitive/physiological analytics. Each interaction aids in customizing the patient user's personal performance profile so that future sessions can be tailored to the personalized needs and recovery typology of the patient user. Active decision analytics may include dynamic 3D asset modification in the 3D rendering, VR hand controller interaction, participation pathing, headset head-tracking position sensor interaction, eye-tracking sensor interaction, decision making interaction, group decision making interaction, duration of gameplay, decision tree with assessments over time, sensor-integrated interaction, intentional body actions (tracked through gesture detection sensor technology), and procedural pathing. Passive cognitive/physiological analytics may include fNIRS analytics, GSR analytics, EEG monitoring, individual performance assessment, Mocap monitoring, body pressure monitoring, electrocardiogram (ECG) monitoring, PET monitoring, and heart rate monitoring. The immersive ecosystem 100 uses active decision analytics and passive cognitive/physiological analytics data to inform the dynamic decision matrix. For example, as described above, AI engine 150 of immersive ecosystem 100 may use active performance analytics and real-time EEG raw sensor data to calculate a neural efficiency score for a user.

Figure 3:
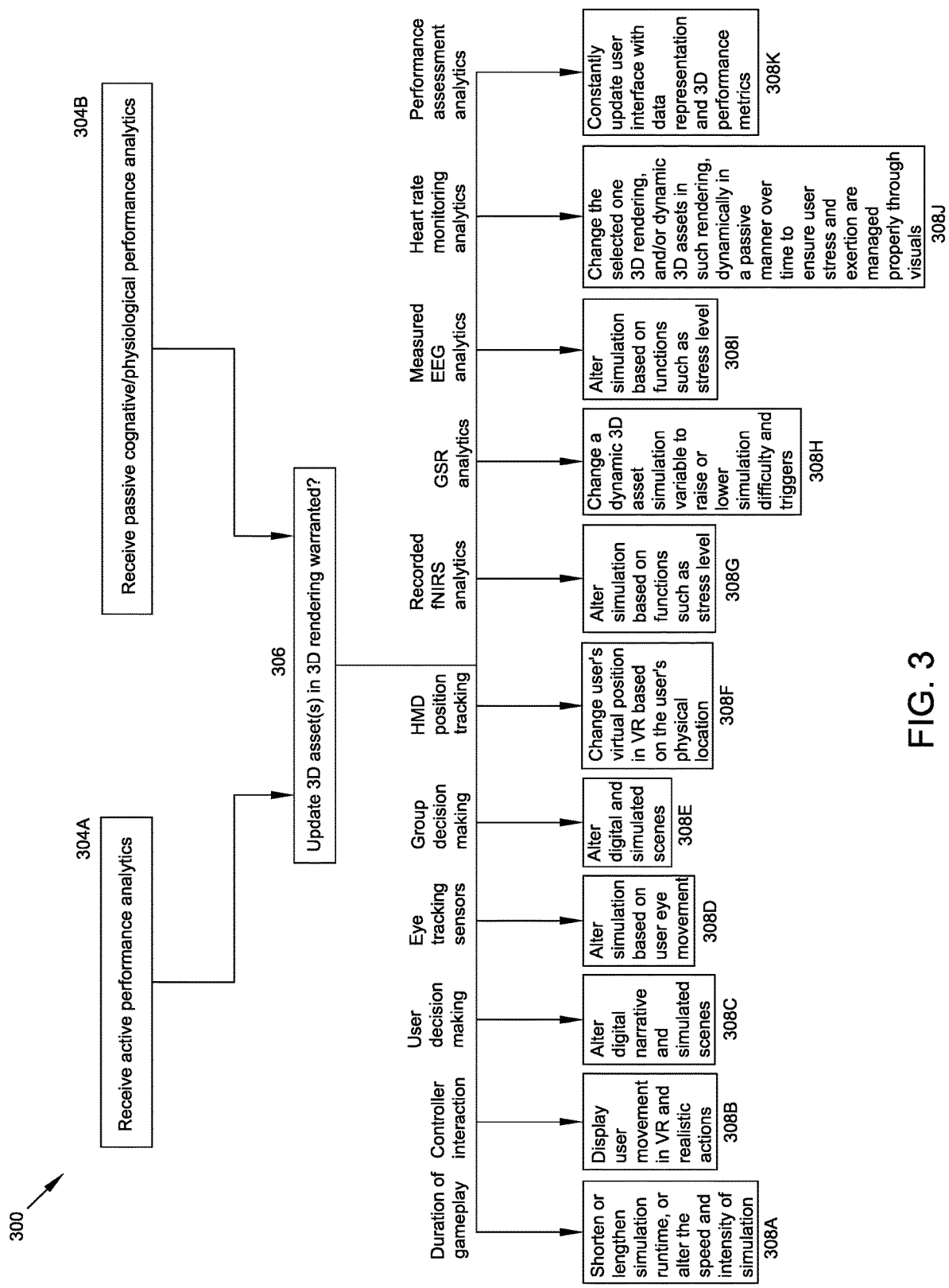
FIG. 3 is a flow chart illustrating a dynamic decision matrix-implemented method according to some embodiments of the present disclosure.

FIG. 3 illustrates a flow chart of an exemplary method 300 performed by a dynamic decision matrix according to some embodiments. The dynamic decision matrix is informed by the personal performance profile data from a cloud or local database 120 and determines what decision the user (e.g. patient user) has the ability to make inside the virtual environment. Live data (e.g. from the current treatment/training session) may be dynamically provided to the dynamic decision matrix so that it is based on current and real circumstances.

As illustrated in FIG. 3, the dynamic decision matrix receives one or more active performance analytics at step 304A and/or one or more passive cognitive/physiological analytics at step 304B. Examples of both the active and passive performance analytics, and resulting dynamic changes in selected one 3D renderings and in dynamic 3D assets in such renderings, are described above in detail. For example, active performance analytics received at step 304A may include, without limitation, duration of gameplay, decision tree with assessments over time, head-mounted display (HMD) tracking position sensor interaction, eye tracking sensor integration, decision making interaction, group decision making interaction, procedural pathing, sensor-integrated interaction, hand controller interaction, intentional body actions (tracked through gesture detection sensor technology), etc. For example, passive cognitive/physiological analytics received at step 304B may include, without limitation, Functional Near-Infrared Spectroscopy (fNIRS) analytics, electroencephalograph (EEG) monitoring, Galvanic Skin Response (GSR) analytics, heart rate monitoring, ECG monitoring, individual performance assessment, etc. At step 306, the dynamic decision matrix determines whether the received active and/or passive performance analytics warrant dynamically updating one or more 3D assets in the selected one 3D rendering.

The following examples of active performance analytics received by the dynamic decision matrix are non-limiting. The dynamic decision matrix may receive analytics on the duration of gameplay and may respond by shortening or lengthening the simulation runtime or altering the speed and intensity of the simulation at step 308A. The dynamic decision matrix may receive analytics on controller interaction (e.g. selection of 3D assets, movement, or specific functions such as teleportation in VR) and may respond by displaying user movement in VR and realistic actions at step 308B. The dynamic decision matrix may receive analytics on user decision making (e.g. choices to perform certain actions in the simulation and participate in specified scenarios) and may respond by altering the digital narrative and simulated scenes at step 308C. The dynamic decision matrix may receive analytics on eye tracking sensors (e.g. intentionally looking in specific directions or reducing sporadic eye movements in virtual scenarios) and may respond by altering the simulation based on user eye movement at step 308D. The dynamic decision matrix may receive analytics on group decision making (e.g. groups of users changing the virtual scene by agreeing upon a choice and selecting options in VR) and may respond by altering the digital narrative and simulated scenes at step 308E. The dynamic decision matrix may receive analytics on head-mounted display (HMD) position tracking (e.g. physically walking in VR throughout virtual environments) and may respond by changing the user's virtual position in VR based on the user's physical location at step 308F.

The following examples of passive performance analytics received by the dynamic decision matrix are non-limiting. The dynamic decision matrix may receive recorded fNIRS analytics (e.g. cognitive activity continuously recorded throughout the simulation) and may respond by altering the simulation based on functions such as stress level at step 308G. The dynamic decision matrix may receive GSR analytics (e.g. neurological and arousal spectrum tracking) and may respond by changing a dynamic 3D asset (e.g. simulation variable) to raise or lower the simulation difficulty and triggers at step 308H. The dynamic decision matrix may receive measured EEG analytics (e.g. cognitive activity continuously measured throughout the simulation) and may respond by altering the simulation based on functions such as stress level at step 308I. The dynamic decision matrix may receive heart rate monitoring analytics and may respond by changing the selected one 3D rendering, and/or dynamic 3D assets in such rendering, dynamically in a passive manner over time to ensure user stress and exertion are managed properly through visuals at step 308J. The dynamic decision matrix may receive performance assessment analytics (e.g. constant user data collection accumulated throughout the simulation) and may respond by constantly updating the user interface with data representations and 3D performance metrics at step 308K.

Based on active (real-time) data feeds from a user's responses to dynamic 3D assets within the 3D rendering, individual and collective analytics may be gathered and provided to the AI engine 150, which may actively adjust the dynamic decision matrix. In the addiction treatment session example, the AI engine 150 may draw curated data points from a patient user's personal performance profile on database 120 to automatically and intelligently generate the appropriate trigger and recovery 3D renderings by modifying at least one of a plurality of dynamic 3D assets in the 3D rendering. Based on the personal performance profile, analytics from the rapid imaging initial assessment may help determine a baseline stress level and the appropriate triggering 3D rendering, and the user responses to the dynamic 3D assets in the triggering 3D rendering may help determine the appropriate recovery 3D rendering. Based on the personal performance profile, neurological analysis, and user responses, the complexity of the 3D rendering may be adjusted. Based on the personal performance profile and analytics on speed, focus, and fNIRS (cognitive mapping), the mental strain caused by the complexity of a triggering 3D rendering or the intensity of a recovery 3D rendering may be adjusted. Dynamic 3D assets such as daylight, weather, location effects, population, and number of patients in the 3D rendering may be modified based on the personal performance profile and analytics on cognitive, physiological, comprehension, speed, focus, and fNIRS data.

After the patient user undergoes the initial assessment, his/her personal performance profile may be formed and stored on database 120, which will be continuously updated as the patient user progresses through therapeutic treatment. In some embodiments, the personal performance profile may be stored on a localized database. Incorporating established metrics for stress levels, the AI engine 150 may analyze the patient user's profile and brain activity metrics to determine the patient user's triggers and the appropriate 3D rendering to display for treatment.

Once the patient user's triggers have been assessed, the AI engine 150 may communicate one of a plurality of pre-determined triggering 3D renderings to the processor 130 for providing to the VR headset (e.g. 110A). In order to determine the appropriate scenic environment that may be used to trigger or aid in the recovery of the patient, the immersive ecosystem 100 may use the following components: a gaming engine, the AI engine 150, and the database 120. The gaming engine may be used to generate 3D environments, structures or facilities, time of day, climate, and weather, as well as 3D atmospherics, objects and models, and media elements and sound effects. The AI engine 150 and database 120 may provide the patient's personal performance profile, AI engine 150 generated dynamic 3D assets and challenge variables, skills and protocol algorithms, and behavioral and sentiment algorithms. The immersive ecosystem 100 will place dynamic 3D assets (e.g. from a library of digital assets) into the 3D rendering at a given time. The placement of dynamic 3D assets for a given session and a given 3D rendering and related behaviors will be variable, dynamic, and informed by the AI engine 150 and the patient user's personal performance profile. Once 3D assets are placed and the logic of a specific 3D rendering is applied, variable attributes may be defined based on the patient's personal performance profile. Non-limiting examples of dynamic 3D assets may include: physical objects, number of people, number of obstacles, number of distractions, time of day, levels of light, type of weather, time to complete the treatment session, placement of objects from hidden to visible (to test for amplitude of sentiment), and sentiment and personality of virtual humans in the 3D rendering. Dynamic 3D assets may be designed and developed within the gaming engine (e.g. Unity™ 3D engine and Unreal® engine).

VR technology 110 may include hardware to allow for room scale VR, enabling patients to walk around and interact with the physical space in a 3D rendering in a realistic and meaningful way. In various embodiments, VR hardware also enables the mapping of layouts of the physical space within the 3D rendering, integration of physical objects, and precise performance tracking.

During the treatment session, the patient user's neural activity may inform and trigger the AI engine 150 to respond to the measured user responses and provide triggering dynamic 3D assets (relevant to the patient user's personal performance profile) to the patient user's VR headset (e.g. 110A). The AI engine 150 actively collects analytic data from live trigger and recovery scenarios. The AI engine 150 may automatically and intelligently generate key insights and use them to adjust the dynamic 3D assets in the patient user's recovery 3D rendering during current and future sessions. The VR headset (e.g. fNIRS-sensored headset, EEG-sensored headset) may map the magnitude of stress evoked from triggering 3D renderings, and the AI engine 150 may suggest recovery 3D renderings as they relate to the patient user's personal performance profile. In some embodiments, the 3D renderings may range from real-life scenarios to abstract therapeutic imagery to help refocus the patient user on feelings of positivity as it pertains to their addiction.

Treatment session results, real-time analytics, and overall milestones for patient users may be tracked using a variety of sensors both in the VR headset as well as external integrations. All metrics may be recorded and auto-synced with the database 120 running the VR treatment session so that the recovery 3D rendering and dynamic 3D assets are adjusted in real-time. The results of each treatment session will be tracked and recorded such that the specialist and/or patient user can view them during the session (in VR) or on a web-based analytics dashboard (e.g. administrator interface 160). In various embodiments, based on a computed neural efficiency score and a comparison with an expected neural efficiency score (e.g. is a computed neural efficiency score higher than a threshold?), a specialist may accelerate the treatment of a particular user.

The immersive ecosystem 100 may comprise a mobile application that utilizes personalization from the patient user's personal performance profile to aid in the patient user's recovery. In various embodiments, the mobile application may use GPS API integration (e.g. open source GPS API) to alert the patient user when he/she is in the vicinity of a physical location that encourages positive cognitive and physiological responses during triggering. The mobile application may be used to frequently remind the patient of circumstantial environments that are likely to create and foster recovery modalities. The inventor has identified that the more the brain is consciously and subconsciously reminded of recovery behavior to replace triggering behaviors, the more likely the patient is to make positive choices. The mobile application may also alert the patient user when they are in a geographic area that may cause triggering based on the patient user's personal performance profile. The mobile application may also offer the user an "escape" by switching to VR mode (e.g. by instructing the user to go to an appropriate location and enable VR technology 110) and providing the user a 3D rendering such as a recovery oriented meditative scene.

The inventor has identified that an immersive ecosystem 100 for treating opioid addiction will be significant because it will help both the specialist and the patient user understand the cognitive status of the patient user during simulated trigger and recovery scenarios. Further, the immersive ecosystem 100 will tailor patient recovery to the individual by allowing the 3D rendering to react to neurological cues to deliver tailored, more effective recovery scenarios.

As mentioned previously, in some embodiments, an exemplary 3D rendering may include a military training environment. The inventor has observed that cognitive performance is a subject of ever-growing concern to the military, and that military growth, protocol complexity, and ever-diminishing resources warrant more efficient training for servicemen and women. During military basic training for recruits, drill instructors are traditionally as intense as possible at all times towards such recruits. However, the inventor has identified that if the training environment pushes a recruit's brain beyond the recruit's peak performance stress level, there is a significant drop-off in the recruit's performance, which wastes time and money in training. The inventor has also identified that an immersive ecosystem 100, and specifically VTAT, may provide a simulated 3D training environment where the dynamic decision matrix may receive recorded fNIRS analytics showing the recruit's stress level, or measured EEG analytics showing the recruit's cognitive load and/or cognitive attention (and/or other passive and/or active analytics). The dynamic decision matrix may compare the received stress level to a predetermined peak performance stress level. If the received stress level exceeds the peak performance stress level, the dynamic decision matrix may modify one or more dynamic 3D assets (e.g. decrease the intensity of a simulated drill instructor) in the training simulation in order to lower the recruit's stress level to his/her peak performance stress level. The inventor has also identified that the immersive ecosystem 100 may be particularly useful for such training because it allows a supervisor to track and ensure that during the training, a recruit stays in his/her personalized spectrum of peak performance.

Figure 7:
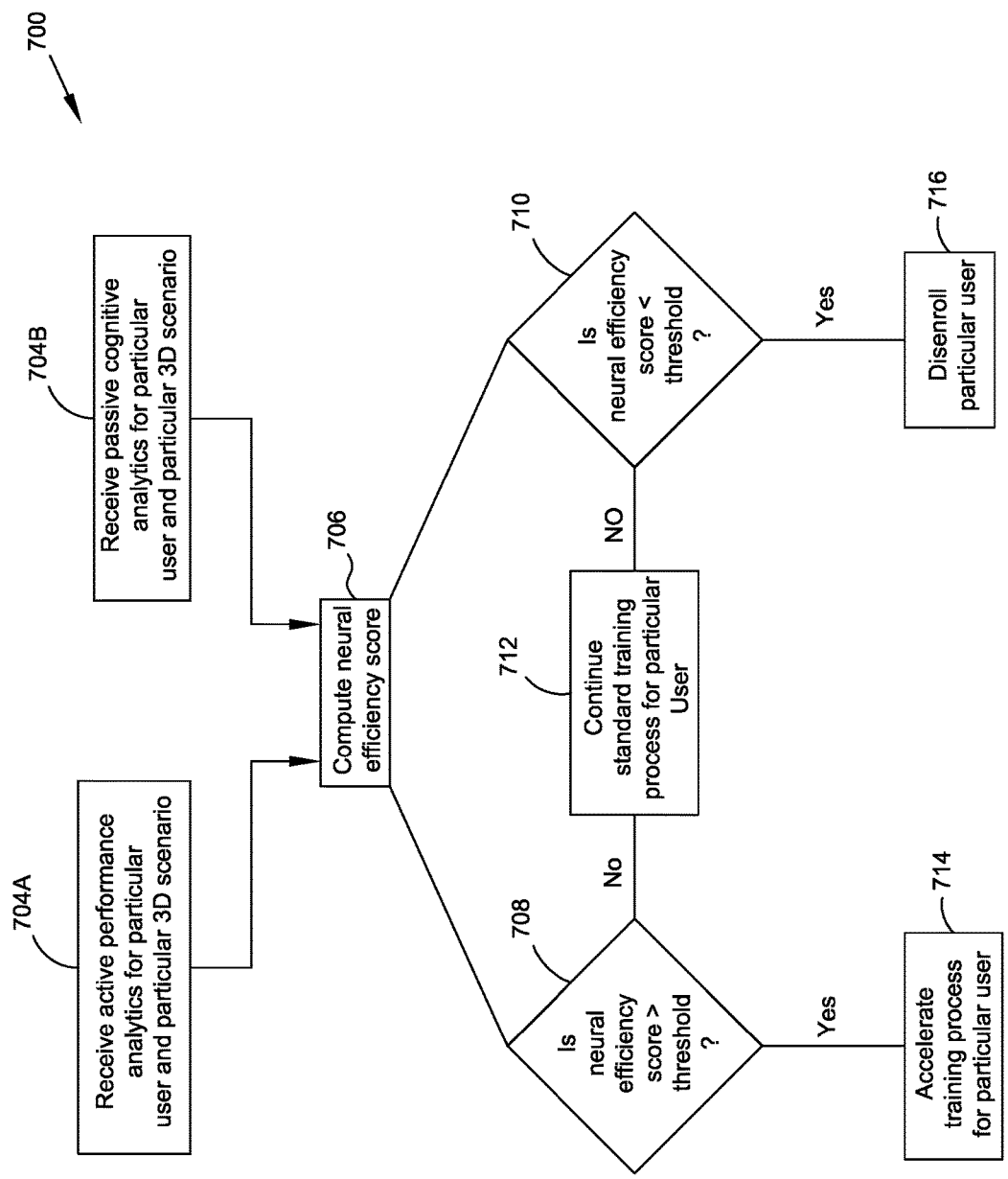
FIG. 7 is a flow chart illustrating an example of an artificial intelligence engine-implemented and leveraged method according to some embodiments of the present disclosure.

Referring now to FIG. 7, a flow chart illustrating an artificial intelligence engine-implemented and leveraged method according to some embodiments of the present disclosure is provided. At block 704A, AI engine 150 may receive active performance analytics for a particular trainee user and a particular 3D training scenario as described above for block 304A. At block 704B, AI engine 150 may receive passive cognitive analytics for the particular trainee user and the particular 3D training scenario (e.g. raw EEG sensor data as described above for block 304B). At block 706, and as described above, AI engine 150 may compute a neural efficiency score for the trainee user. At block 708, AI engine 150 may determine whether the computed neural efficiency score for the trainee user is greater than a threshold (e.g. an expected neural efficiency score for the particular 3D scenario). At block 714, if the computed neural efficiency score for the trainee user is determined to be greater than a threshold, then AI engine 150 may accelerate the training process for a particular trainee user via the dynamic decision matrix (e.g. FIG. 3) and/or provide a recommendation to the training administrator (e.g. via administrator interface 160) that the training process for a particular trainee user be accelerated. If the computed neural efficiency score for the trainee user is determined (at block 708) to be less than or equal to the threshold, then, at block 712, AI engine 150 may continue the standard training process for the particular trainee user via the dynamic decision matrix (e.g. FIG. 3). At block 710, AI engine 150 may determine whether the computed neural efficiency score for the trainee user is lower than a threshold (e.g. an acceptable neural efficiency score for the particular 3D scenario). At block 716, if the computed neural efficiency score for the trainee user is determined to be less than (or equal to) another threshold, then AI engine 150 may provide a recommendation to the training administrator (e.g. via administrator interface 160) that the particular trainee user be disenrolled from the training process. If the computed neural efficiency score for the trainee user is determined (at block 710) to be greater than the threshold, then, at block 712, AI engine 150 may continue the standard training process for the particular trainee user via the dynamic decision matrix (e.g. FIG. 3).

The results of each training simulation may also be tracked and recorded such that the trainee and/or trainer can respectively view them during the session (in VR headset 110A) or on a web-based analytics dashboard (e.g. administrator interface 160). In various embodiments, the VTAT may include a forensics module including a recording feature that would allow instructors to record the results of the user's training session (e.g. record, throughout the duration of the 3D scenario, the received active performance analytics (e.g. 304A, 704A), the received passive performance analytics (e.g. 304B, 704B), the 3D assets in the 3D rendering experienced by the user in the VR headset, etc.) and then subsequently playback (e.g. rewind and view) such training simulation sessions. In various embodiments, utilizing the neurological data analytics visualization (e.g. analytics dashboard), instructors can demonstrate and point out areas where users experienced stressful responses during the particular 3D scenario (e.g. VR/AR/XR simulation session). As described herein, in various embodiments, the AI engine 150 calculation of real-time neural efficiency scores throughout particular 3D scenarios provides instructors with objective data to enable instructors to make better decisions, and more accurately evaluate trainees, instead of relying on conventional, subjective assessment. Currently, subjective assessment is used heavily by trainees and instructors in the military and in law enforcement. The inventor has observed that these conventional subjective assessment processes are flawed, frequently produce skewed results, and make challenging both conventional methods of comparing trainees, and conventional methods of comparing various training simulation systems.

The inventor has determined that the immersive ecosystem 100 and, in particular, the VTAT enables instructors/trainers (or other end users) to objectively visualize trainee progression over time during various 3D training scenarios. By evaluating individual trainee scores (e.g. stress scores, proficiency scores, neural efficiency scores) against predefined baselines relevant to particular immersive tasks (VR, AR, XR), the inventor has determined that the AI engine 150 can show individualized progression in the process of a trainee user growing accustomed to specific situations. In this manner of personalized development, the inventor has determined that trainee users are able to develop targeted traits as they pertain to given simulation environments and virtualized tasks in immersive simulations (VR, AR, XR) via immersive ecosystem 100. The inventor has also determined that this ability of trainee users to develop such targeted traits is significant because it allows trainers/instructors or other end users to visually evaluate and further predict affecting patterns of neural activity (e.g. stress, focus) and the external factors that induce these patterns. As described herein, this is actionable data that can be built upon in a number of ways to increase or decrease neurocognitive responses, increase or decrease individualized affecting patterns, and increase or decrease stress attribution to any environment variables that cause particular stimuli. Due to user-specific score ranges (e.g. stress scores, proficiency scores, neural efficiency scores) matched against predefined baselines, trainers/instructors or other end users are able to assess the present state of mind and cognition of users during particular events, locate and identify user-specific triggering variables, and objectively quantify the effectiveness of various training simulations and compare such various training simulations. In a military training environment, for example, the inventor has determined that this ultimately increases training speed and decision making-quality, as trainers/instructors are able to confidently pass trainees based on a combination of their neural efficiency scores (described above) and technical performance.

In some embodiments, the user may be a military trainee participating in a training simulation where an exemplary 3D rendering may include one or more military training 3D renderings. In this example, the immersive ecosystem 100 may provide an immersive VR, AR, or XR training solution that adapts to each trainee. By integrating adaptive architecture and a native feedback loop of trainee biometric, physiological, neural efficiency, and performance data (via dynamic decision matrix), the inventor has determined that AI engine 150 may significantly cut training costs by allowing virtual environments within VR, AR, or XR training simulations to be authored automatically by combined AI and machine learning algorithms. The inventor has also determined that VTAT, including the dynamic decision matrix of AI engine 150, eliminates the need to spend extra time and money creating massive amounts of modules in order to evaluate user performance on different difficulty levels. Instead, the inventor has determined that VTAT, including the dynamic decision matrix of AI engine 150, enables trainers to accomplish immersive scene authoring dynamically and during the real-time 3D simulations.

In this example, the dynamic decision matrix may control two major VR, AR, or XR dynamic 3D assets (e.g. simulation difficulty and speed) and their affecting variables. In various embodiments, the AI engine 150 may use machine learning algorithms based on principles of neuroscience and the effect of task complexity on cognitive performance (e.g. determined neural efficiency scores) to determine how to adjust these dynamic 3D assets and their affecting variables via the dynamic decision matrix. For example, as described above (FIG. 3), the AI engine 150 may control the difficulty of a simulation process by manipulating preset task parameters (e.g. the complexity of tasks). As also described above (FIG. 3), the AI engine 150 may manipulate the virtual environment during task performance by changing affecting behavior patterns of dynamic 3D assets within the 3D rendering. In the case of complexity, the updating of dynamic 3D assets in a 3D rendering may include object position.

Figure 5:
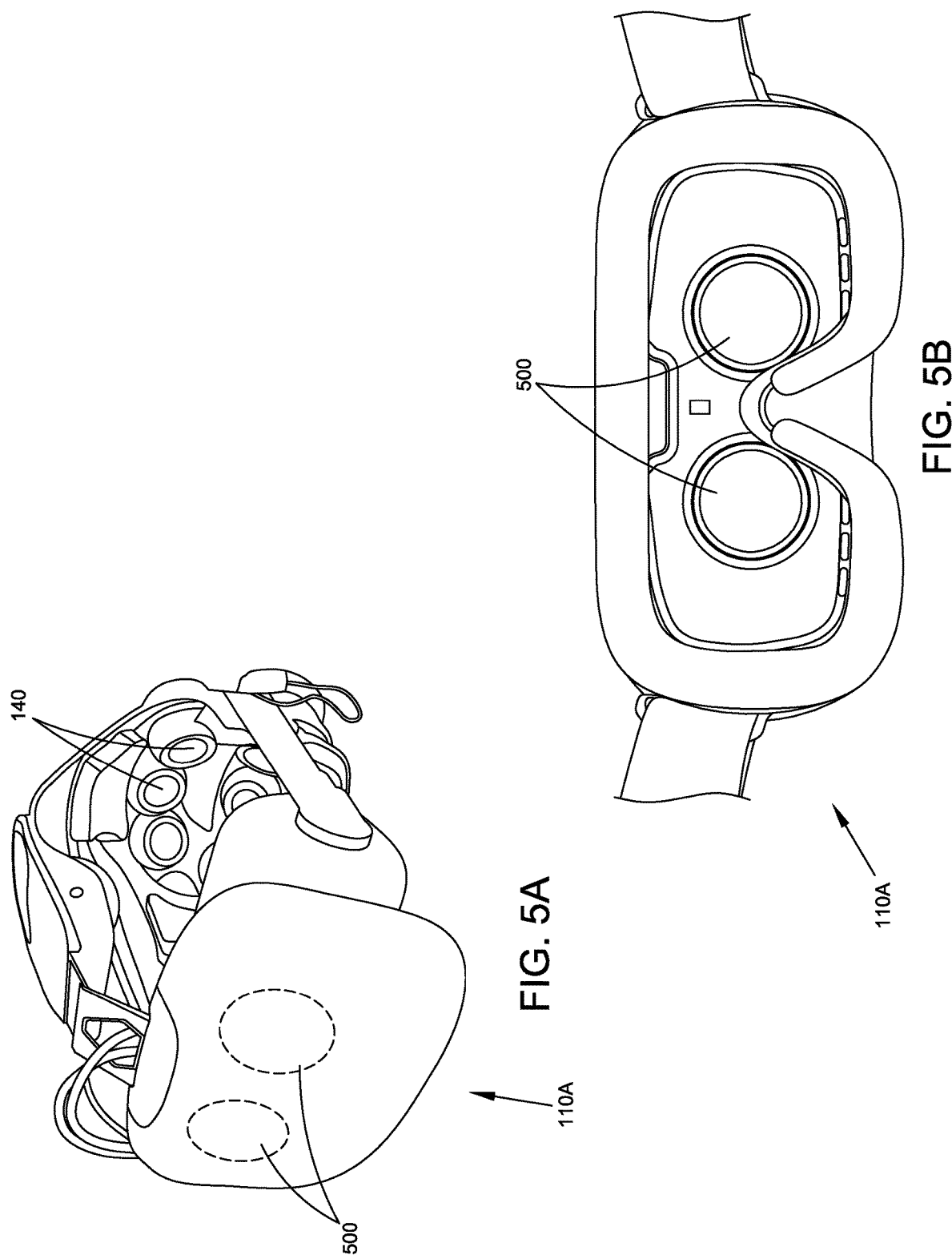
FIG. 5A is a front view of an example of a virtual reality headset according to some embodiments of the present disclosure.
FIG. 5B is a partial view of a front interior of an example of a virtual reality headset according to some embodiments of the present disclosure.
Figure 6:
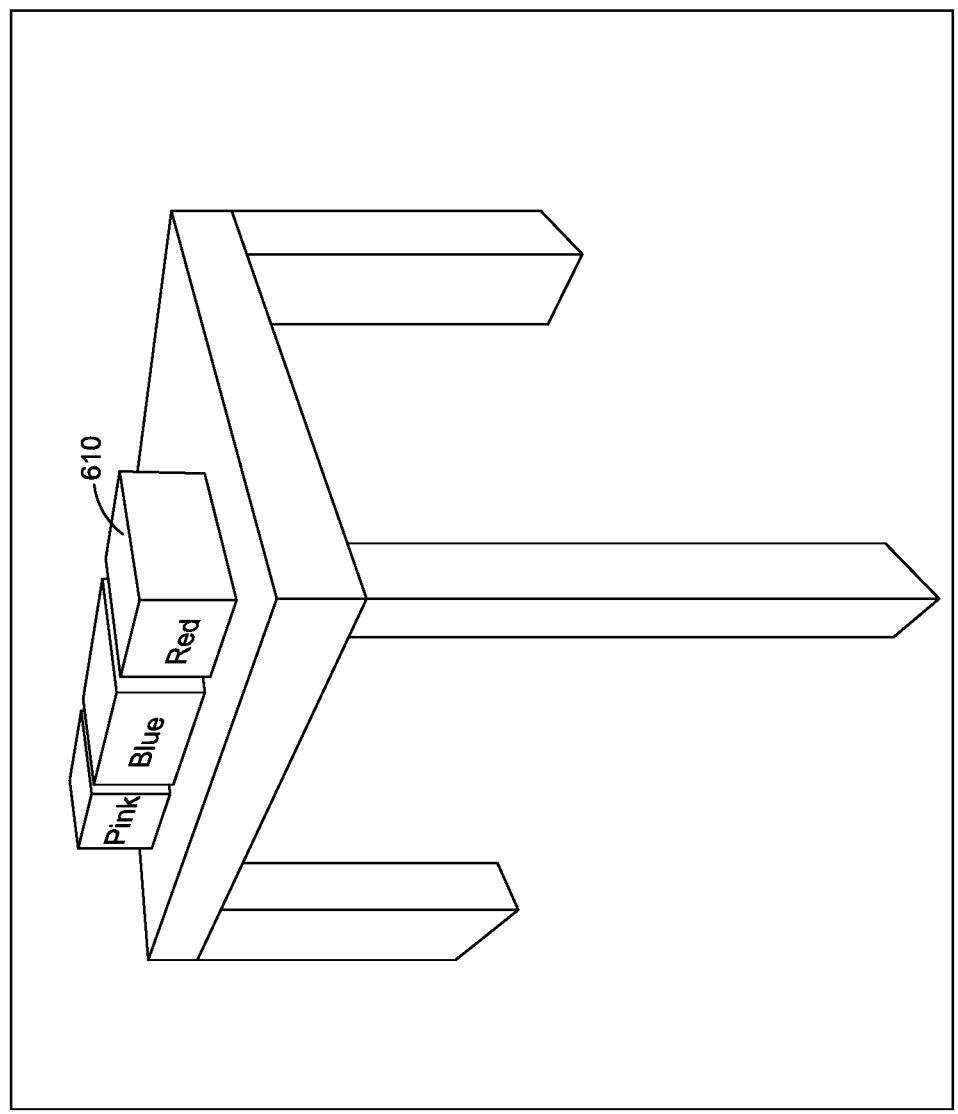
FIG. 6 is a diagram showing an example of a virtual reality 3D rendering according to some embodiments of the present disclosure.

For example, a virtual training simulation may require users to sort boxes (3D assets 610) on a conveyor belt based on the color of the word written on each box. This may be a Stroop Color and Word Test that requires users to view boxes (3D assets 610) at particular angles. This example is illustrated in FIG. 6, which shows an exemplary 3D rendering 600, which includes multiple exemplary 3D assets 610 (e.g. boxes, conveyer belt, words, etc.). The angle and positional data of each box (3D asset 610) in the 3D rendering 600 can be automatically changed to make the it more difficult or easier to view the written word (3D asset 610) on each box based on the neural data that the AI engine 150 receives on each trainee in real-time. A user may view the 3D rendering 600 using a VR headset 110A illustrated in FIGS. 5A and 5B. FIG. 5A shows a front view of an exemplary VR headset 110A, which includes sensors 140 and goggles 500. Goggles 500 are illustrated in further detail in FIG. 5B, which shows a partial view of a front interior of VR headset 110A. When wearing VR headset 110A, a user may look through goggles 500 to see 3D rendering 600 in order to participate in a virtual training simulation like the Stroop Color and Word Test.

As described above (e.g. 308A, FIG. 3), the AI engine 150 may also automatically change the speed at which a virtual task requires completion by the trainee. In various embodiments, passive data recording (e.g. at block 304B, 704B and via forensics module of AI engine 150) may be accomplished over longer periods of time (e.g., longer 3D scenarios, over a plurality of 3D renderings within a training module) and may provide more actionable neural data readouts. In various embodiments, as described above (e.g. 308A, 308G, 308H, 308I, 308J, FIG. 3), the AI engine 150 may be programmed to automatically recognize when users require longer periods of time to complete a simulation within a 3D rendering (e.g. 600) based on their stress response and how their real-time neural states are being affected by the virtual task at hand. In various embodiments, as described above (e.g. 308A-308K, FIG. 3), the AI engine 150 also controls the individualized speed of dynamic 3D assets 610 within the 3D rendering 600 of these training modules. In the case of the Stroop Color and Word Test example, a dynamic 3D asset 610 behavior component may be coded in AI engine 150 to regulate the speed at which these assets 610 accelerate and decelerate. In various embodiments, as described above (e.g. 308A, 308G, 308H, 308I, 308J, FIG. 3), dynamic decision matrix may affect dynamic 3D asset 610 behavior and speed based on real-time measured trainee neural data (e.g. stress response). For example, for the Stroop Color and Word Test example, the rate at which boxes (3D assets 610) on the conveyor belt move towards the trainees in the 3D rendering 600 may be controlled by the direct stress response of trainees as described above (e.g. 308A, 308G, 308H, 308I, 308J, FIG. 3).

In some embodiments, the sensors 140 may include an EEG sensor array in a VR HMD (e.g. 110A). In various embodiments, an EEG sensor array may include a VR-compatible brain-sensing device with a plurality of dry EEG sensors. In various embodiments, an EEG sensor array may include wet EEG sensors or any suitable EEG sensors. As described above, these EEG sensors 140 may provide an input to a neural efficiency calculation for a trainee who is performing a task in a 3D rendering 600 of a VR scenario. During this scenario, the AI engine 150 can identify, on a training timeline, when the trainee is significantly stressed or losing attention. In various embodiments, the AI engine 150 uses algorithms to predict the virtual stressors that occur within simulations and, using the dynamic decision matrix as described above (e.g. 308A, 308G, 308H, 308I, 308J, FIG. 3), dynamically adjusts one or more dynamic 3D assets 610 in the 3D rendering 600 to ensure the difficulty and complexity of the simulation results in trainees performing their tasks at a peak performance level.

In various embodiments, as described above, the immersive ecosystem 100 can pull in many different active performance, passive cognitive, passive physiological, and/or passive performance data points throughout the training experience and may include a custom analytic dashboard for this data and other data (e.g. computed neural efficiency scores) (e.g. via administrator interface 160). In various embodiments, the immersive ecosystem 100 may also integrate with an existing Learning Management System (LMS). In some embodiments, data points within a LMS can be based on results obtained for a trainee user via immersive ecosystem 100 (e.g. the trainees' ability to complete specific tasks within a 3D rendering 600 of a virtual training module). In some embodiments, data points within a LMS can be based on cognitive load, biometric/physiological indicators, eye tracking, motion capture, and a variety of other data types obtained for a trainee user via immersive ecosystem 100. The inventor has identified that a particular benefit of certain embodiments of immersive ecosystem 100 includes its ability to display both real-time and recorded trainee results (e.g. through a VTAT, which may provide performance data to trainers through an analytics dashboard and to trainees through their VR HMD).

Although examples are illustrated and described herein, embodiments are nevertheless not limited to the details shown, since various modifications and structural changes may be made therein by those of ordinary skill within the scope and range of equivalents of the claims.

What is claimed is:

1. An immersive training system comprising:
one or more sensors configured to measure at least one response of a user to a three-dimensional (3D) asset of a 3D rendering that is being rendered on a virtual reality (VR) display, the 3D rendering comprising a plurality of 3D assets;
a processor;
a non-transitory computer-readable medium; and
a set of instructions stored on the computer-readable medium that is operable when executed on the processor to:
generate a personal performance profile specific to the user and based on prior stored measured user responses to one or more 3D assets of the plurality of 3D assets of the 3D rendering;
receive, in real-time, the at least one measured response of the user to the 3D asset,
update the user-specific personal performance profile based on the received at least one measured response of the user to the 3D asset;
compare, in real-time, the received at least one measured response of the user at a given time with a corresponding predetermined user response value to the 3D asset at a corresponding predetermined time value to the 3D asset;
generate a dynamic decision matrix customized for the user based on the user-specific personal performance profile and a neural efficiency score of the user, and
modify, in real-time, at least one of the plurality of 3D assets of the 3D rendering based on the dynamic decision matrix customized for the user and the user response comparison.

2. The immersive training system of claim 1, wherein the one or more sensors comprises:
an active sensor configured to measure a physical response of the user to the 3D asset; or
a cognitive or physiological sensor configured to measure a passive cognitive or passive physiological response of the user to the 3D asset.

3. The immersive training system of claim 1, wherein the one or more sensors comprises:
an active sensor configured to measure a physical response of the user to the 3D asset; and
a cognitive or physiological sensor configured to measure a passive cognitive or passive physiological response of the user to the 3D asset, and
wherein the set of instructions stored on the computer-readable medium being further operable when executed on the processor to generate the neural efficiency score of the user based on:
a proficiency score determined, in real-time, based on a comparison between the measured physical response of the user to the 3D asset and a corresponding measurement of correctness, and the measured passive cognitive or passive physiological response of the user to the 3D asset.

4. The immersive training system of claim 1, wherein the corresponding predetermined user response value to the 3D asset is determined, in part, based on an experience level of the user, a training level of the user, or the neural efficiency score of the user.

5. The immersive training system of claim 3, wherein the set of instructions stored on the computer-readable medium being further operable when executed on the processor to modify, in real-time, the at least one of the plurality of 3D assets of the 3D rendering based on a comparison between the generated user neural efficiency score and a neural efficiency threshold.

6. The immersive training system of claim 1, wherein the generated user-specific personal performance profile is further based on one or more of: demographic information of the user, addiction history of the user, an emotional and personality profile of the user, program objectives for the 3D rendering, and feedback from a trainer observing the user's performance.

7. The immersive training system of claim 3, wherein the at least one of the plurality of 3D assets of the 3D rendering is further modified to maintain the measured passive cognitive or passive physiological response of the use rat a predetermined peak performance stress level.

8. The immersive training system of claim 2, wherein the cognitive or physiological sensor comprises one or more of: functional near-infrared spectroscopy (fNIRS) technology, electroencephalogram (EEG) technology, an electrocardiogram (ECG) sensor, a heart rate sensor, and galvanic skin response (GSR) technology, or wherein the active sensor comprises one of: a motion capture (Mocap) sensors, an eye tracker sensor, and a body pressure sensor.

9. The immersive training system of claim 1, wherein the 3D rendering that is being rendered on the VR display is during a VR scenario, and wherein the set of instructions stored on the computer-readable medium is further operable when executed on the processor to:
receive the at least one measured response of the user during the VR scenario,
compare, during the VR scenario, the received at least one measured response of the user at a given time with the corresponding predetermined user response value to the 3D asset at a corresponding predetermined time value of the VR scenario; and
modify the at least one of the plurality of 3D assets of the 3D rendering during the VR scenario.

10. The immersive training system of claim 9, wherein the corresponding predetermined user response value is pre-programmed in a cloud-based database, and the corresponding predetermined time value is pre-programmed on the computer-readable medium.

11. The immersive training system of claim 9, wherein the corresponding predetermined user response value, and the corresponding predetermined time value, are pre-programmed in a cloud-based database.

12. A computer-implemented method for immersive training comprising:
measuring, with one or more sensors, at least one response of a user to a three-dimensional (3D) asset of a 3D rendering that is being rendered on a virtual reality (VR) display, the 3D rendering comprising a plurality of 3D assets; and
executing, on a processor, a set of instructions stored on a computer readable medium that is operable to:
generate a personal performance profile specific to the user and based on prior stored measured user responses to one or more of the 3D assets of the plurality of assets of the 3D rendering;
receive, in real-time, the at least one measured response of the user to the 3D asset,
update the user-specific personal performance profile based on the at least one measured response of the user to the 3D asset;
compare, in real-time, the received at least one measured response of the user at a given time with a corresponding predetermined user response value at a corresponding predetermined time value to the 3D asset;

generate a dynamic decision matrix customized for the user based on the user-specific personal performance profile and a neural efficiency score of the user, and modify, in real-time, at least one of the plurality of 3D assets of the 3D rendering based on the dynamic decision matrix customized for the user and the user response comparison.

13. The computer-implemented method of claim 12, wherein the one or more sensors comprises:

an active sensor configured to measure a physical response of the user to the 3D asset; or a cognitive or physiological sensor configured to measure a passive cognitive or passive physiological response of the user to the 3D asset.

14. The computer-implemented method of claim 11, wherein the one or more sensors comprises:

an active sensor configured to measure a physical response of the use r to the 3D asset; and a cognitive or physiological sensor configured to measure a passive cognitive or passive physiological response of the user to the 3D asset, and wherein the set of instructions stored on the computer readable-medium being further operable when executed on the processor to generate the neural efficiency score of the user based on:

a proficiency score determined, in real-time, based on a comparison between the measured physical response of the user to the 3D asset and a corresponding measurement of correctness, and the measured passive cognitive or passive physiological response of the user to the 3D asset.

15. The computer-implemented method of claim 12, wherein the predetermined user response value is determined, in part, based on an experience level of the user, a training level of the user, or a neural efficiency score of the user.

16. The computer-implemented method of claim 14, wherein the set of instructions stored on the computer-readable medium being further operable when executed on the processor to: modify, in real-time, the at least one of the plurality of 3D assets of the rendering based on a comparison between the generated user neural efficiency score and a neural efficiency threshold.

17. The computer-implemented method of claim 12, wherein the generated personal performance profile specific to the user is further based on one or more of: demographic information of the user, addiction history of the user, an emotional and personality profile of the user, program objectives for the 3D rendering, and feedback from a trainer observing the user's performance.

18. The computer-implemented method of claim 14, wherein the at least one of the plurality of 3D assets of the 3D rendering is further modified to maintain the measured passive cognitive or passive physiological response of the user at a predetermined peak performance stress level.

19. The computer-implemented method for immersive training of claim 12, wherein the 3D rendering that is being rendered on the VR display is during a VR scenario, and wherein the set of instructions stored on the computer-readable medium is further operable to:

receive the at least one measured response of the user during the VR scenario, compare, during the VR scenario, the received at least one measured response of the user at a given time with the corresponding predetermined user response value to the 3D asset at a corresponding predetermined time value of the VR scenario; and modify the at least one of the plurality of 3D assets of the 3D rendering during the VR scenario.

20. A non-transitory computer-readable medium comprising a set of instructions stored thereon, the set of instructions being operable when executed on a processor to:

receive, in real-time, from one or more sensors, at least one measured response of a user to a three-dimensional (3D) asset of a 3D rendering that is being rendered on a virtual reality (VR) display, the 3D rendering comprising a plurality of 3D assets;

generate a personal performance profile specific to the user and based on prior stored measured user responses to one or more of the 3D assets of the plurality of assets of the 3D rendering;

update the user-specific personal performance profile based on the at least one measured response of the user to the 3D asset;

compare, in real-time, the received at least one measured response of the user at a given time with a corresponding predetermined user response value to the 3D asset at a corresponding predetermined time value to the 3D asset;

generate a dynamic decision matrix customized for the user based on the user-specific personal performance profile and a neural efficiency score of the user; and modify, in real-time, at least one of the plurality of 3D assets of the 3D rendering based on the dynamic decision matrix customized for the user and the user response comparison.

* * * * *